(12) United States Patent
Zhang et al.

(10) Patent No.: US 11,501,441 B2
(45) Date of Patent: Nov. 15, 2022

(54) BIOMARKER DETERMINATION USING OPTICAL FLOWS

(71) Applicant: AIC Innovations Group, Inc., New York, NY (US)

(72) Inventors: Li Zhang, Princeton, NJ (US); Isaac Galatzer-Levy, Brooklyn, NY (US); Vidya Koesmahargyo, Forest Hills, NY (US); Ryan Scott Bardsley, Manchester, NH (US); Muhammad Anzar Abbas, Brooklyn, NJ (US); Lei Guan, Jersey City, NJ (US)

(73) Assignee: AIC Innovations Group, Inc., New York, NY (US)

( * ) Notice: Subject to any disclaimer, the term of this patent is extended or adjusted under 35 U.S.C. 154(b) by 0 days.

(21) Appl. No.: 15/931,483

(22) Filed: May 13, 2020

(65) Prior Publication Data

US 2020/0364868 A1    Nov. 19, 2020

Related U.S. Application Data

(60) Provisional application No. 62/847,793, filed on May 14, 2019.

(51) Int. Cl.
*G06T 7/20*     (2017.01)
*G06T 7/00*     (2017.01)
*G06T 7/246*    (2017.01)
*A61B 5/11*     (2006.01)
*G06V 40/16*    (2022.01)
*G06N 3/04*     (2006.01)

(52) U.S. Cl.
CPC .......... *G06T 7/0016* (2013.01); *A61B 5/1101* (2013.01); *G06T 7/248* (2017.01); *G06V 40/174* (2022.01); *G06N 3/04* (2013.01)

(58) Field of Classification Search
CPC .... G06T 7/0016; G06T 7/248; G06K 9/00302
See application file for complete search history.

(56) References Cited

U.S. PATENT DOCUMENTS

2018/0204314 A1*  7/2018  Kaplanyan ................ G06T 1/20
2020/0086858 A1*  3/2020  Yao .................... B60W 30/0956

OTHER PUBLICATIONS

Herath et al., "Going deeper into action recognition: a survey," arxiv.org, Cornell University Library, 2016, 1 page.
International Search Report and Written Opinion in International Appln. No. PCT/US2020/032839, dated Aug. 20, 2020, 14 pages.
Soran et al., "Tremor detection using motion filtering and SVM," International Conference on Pattern Recognition, 2012, 178-181.
Upchurch et al., "Deep feature interpolation for image content changes," arxiv.org, Cornell University Library, 2016, p. 8.

* cited by examiner

*Primary Examiner* — Sam Bhattacharya
(74) *Attorney, Agent, or Firm* — Fish & Richardson P.C.

(57) ABSTRACT

A computer-implemented method includes obtaining a video of a subject, the video including a plurality of frames; generating, based on the plurality of frames, a plurality of optical flows; and encoding the plurality of optical flows using an autoencoder to obtain a movement-based biomarker value of the subject.

16 Claims, 12 Drawing Sheets

BIOMARKER DETERMINATION USING OPTICAL FLOWS

CROSS-REFERENCE TO RELATED APPLICATIONS

This application claims priority to U.S. Provisional Patent Application Ser. No. 62/847,793 filed on May 14, 2019, the contents of which are incorporated here by reference in their entirety.

BACKGROUND

Tracking and predicting movement of subjects by computer vision or by human raters has been a difficult problem. Small changes in such movement are often too small and irregular to be captured and recognized. Further, categorization of such movement has been difficult.

SUMMARY

The present disclosure relates to determining biomarkers based on video of a subject.

In one aspect, the present disclosure describes a method that includes: obtaining a video of a subject, the video including a plurality of frames; generating, based on the plurality of frames, a plurality of optical flows; and encoding the plurality of optical flows using an autoencoder to obtain a movement-based biomarker value of the subject.

Implementations of the method may include one or more of the following. In some implementations, the movement-based biomarker value includes a frequency of tremor of the subject. In some implementations, the method includes encoding the plurality of optical flows using the autoencoder to obtain a type of tremor of the subject. In some implementations, the type of tremor includes a hand position of the subject. In some implementations, the method includes encoding the plurality of optical flows using the autoencoder to obtain a biomarker type corresponding to the movement-based biomarker value. In some implementations, the biomarker type includes a facial muscle group of the subject.

In some implementations, the method includes generating a plurality of reconstructed optical flows based on an output of the autoencoder, the output including the movement-based biomarker value; and training the autoencoder based on a comparison of the plurality of reconstructed optical flows to the plurality of optical flows. In some implementations, the method includes generating a plurality of reconstructed optical flows using an adversarial autoencoder network, the plurality of reconstructed optical flows based on random samples drawn from a prior distribution used to train the autoencoder in an adversarial discrimination process, and training the autoencoder using the plurality of reconstructed optical flows.

In some implementations, the method includes obtaining a second plurality of optical flows, the second plurality of optical flows being labeled; performing one or more of random translation, random rotation, random scaling, and random cropping on the second plurality of optical flows, to generate an augmenting plurality of optical flows; and training the autoencoder using the augmenting plurality of optical flows. In some implementations, the method includes training the autoencoder using an adversarial discriminator, including: comparing, by the adversarial discriminator, an output of the autoencoder, the output including the movement-based biomarker value, to a distribution; and updating parameters of the autoencoder based on a difference between the output of the autoencoder and the distribution.

In some implementations, the method includes training the autoencoder using labeled data. In some implementations, the labeled data includes experimentally-derived data, the experimentally-derived data including data generated by stimulating a second subject with stimulation having a known frequency. In some implementations, the labeled data is labeled with a biomarker type, and training the autoencoder includes training the autoencoder to determine a biomarker value based on implicit training. In some implementations, the labeled data is labeled with a biomarker value, and training the autoencoder includes training the autoencoder to determine a biomarker type based on implicit training.

In some implementations, generating the plurality of optical flows includes: processing the video with one or more of filtering, noise-reduction, or standardization, to generate a plurality of processed video frames; and generating the plurality of optical flows based on the plurality of processed video frames. In some implementations, the method includes generating the plurality of optical flows based on respective pairs of frames of the plurality of frames. In some implementations, encoding the plurality of optical flows includes: generating one or more optical flow maps based on the plurality of optical flows; and encoding the one or more optical flow maps using the autoencoder to obtain the movement-based biomarker value of the subject.

Particular embodiments of the subject matter described in this specification can be implemented to realize one or more of the following advantages. In some implementations, movement-based biomarkers may be determined more accurately and/or reliably. In some implementations, training data is augmented, such that autoencoder training is improved. In some implementations, optical flows that provide more useful training data for an autoencoder may be generated using an adversarial autoencoder network. In some implementations, an amount of training data required for autoencoder training may be decreased. In some implementations, more useful training data may be obtained experimentally.

The details of one or more implementations are set forth in the accompanying drawings and the description below. Other features and advantages will be apparent from the description and drawings, and from the claims.

DETAILED DESCRIPTION

The present disclosure relates generally to the field of analyzing and quantifying movement. In a particular example, this disclosure relates to analyzing movement in a video to obtain biomarkers of a subject. In a more particular example, this disclosure relates to using optical flow analysis and combined with the use of an autoencoder, in order to obtain biomarkers of a subject.

Biomarkers are quantifiable characteristics of health. They are used to identify disease states and assess treatment response. Biomarkers may include visual, auditory, and movement characteristics of a subject.

Tremors are often used as a biomarker in order to diagnose a disease or a condition in a subject. The presence of tremors, or a change in tremor prevalence and/or magnitude over time (for example, a physical amplitude of a tremor, or a tremor frequency), may be used to diagnose a variety of conditions, including multiple sclerosis, stroke, and Parkinson's disease.

Tremors may be detected by observation, e.g., by a doctor observing a subject during a medical checkup. However, observation-based biomarker detection, including the detection of tremors, may be subjective, such that the same physical biomarker characteristics are recorded differently by different doctors or by the same doctor at different times. In addition, while doctors may be able to perform qualitative evaluation of biomarkers, quantitative biomarker analysis may require analysis aided by video and/or computer technology. For example, determining a frequency of tremor may be difficult or impossible for an unaided doctor.

In some implementations, video analysis may be performed in order to extract movement-based biomarkers. The video analysis may be formulated as a dimension reduction or feature extraction problem. That is, high-dimensional video is encoded into a feature vector with a smaller number of components, the components representing the biomarker. For example, the components may represent a type of movement and a frequency of movement.

In accordance with the various embodiments of the present disclosure, improved methods and systems are provided for obtaining movement-based biomarkers using a combination of an optical flow analysis and an autoencoder process.

Figure 1:
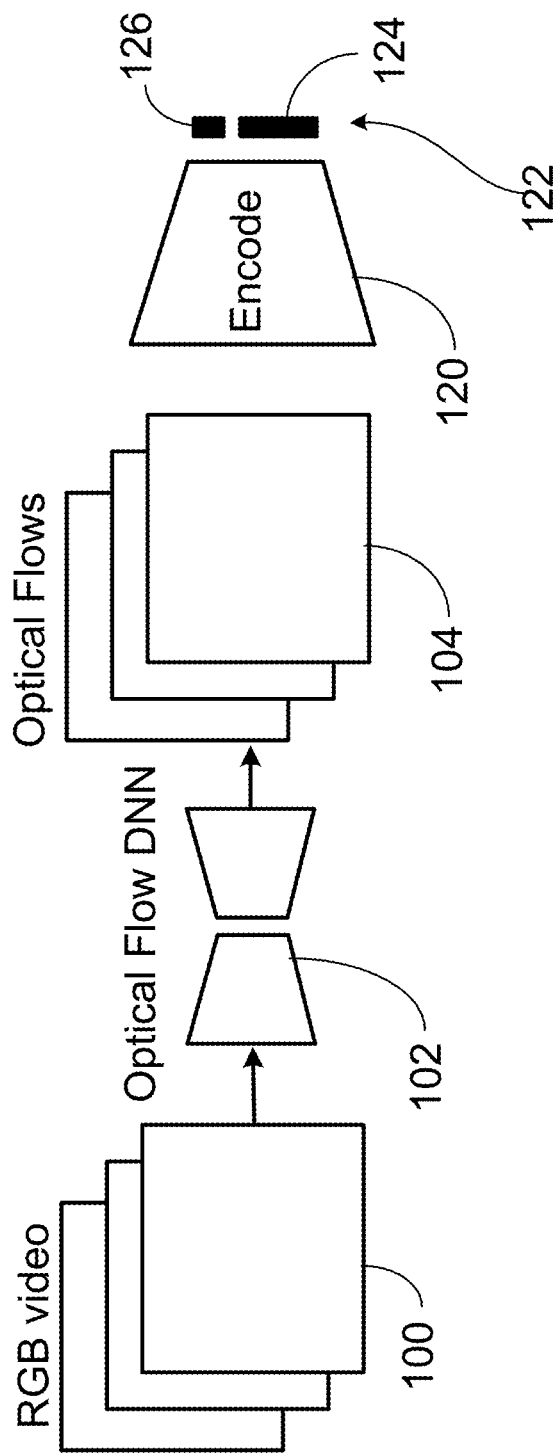
FIG. 1 is a flow chart of exemplary optical flow processing

FIG. 1 shows an example of a process flow for extracting movement-based biomarkers from a video of a subject. First, a video 100 (for example, an RBG video) of the subject is collected. A video dynamic extraction process is then performed on the collected video 100 by a neural network, such as an optical flow deep neural network (DNN) 102, to extract one or more optical flows 104 from the video 100.

In any of the implementations disclosed herein, a video may represent labeled data (e.g., for use in training and/or autoencoder evaluation) or unlabeled data (e.g., video of a subject under medical examination).

In any of the implementations discussed herein, optical flows may include dynamic characteristics of a video and entirely or substantially exclude background and static information of the video. Optical flows may emphasize and/or isolate dynamic features of the video. For example, DNN 102 may extract the optical flows 104 based on a comparison of brightness and/or colors of pixels and/or shapes across frames of the video 100. The analysis performed by the DNN 102 may include, for example, tracking a movement of a given pixel (as represented by a brightness and/or a color of the pixel) from a first frame to a second frame.

In some implementations, optical flows are extracted based on analysis of pairs of frames of a video (for example, adjacent frames of the video 100).

In some implementations, a video or elements of a video (e.g., frames of the video 100) may be processed before optical flows are extracted. For example, the video 100 may be processed with one or more of filtering, noise-reduction, or standardization (e.g., aspect-ratio standardization or resolution standardization to match a standard to which an autoencoder is trained).

In some implementations, a different technique may be used instead of, or in addition to, the DNN 102, in order to extract the optical flows 104. For example, a predefined algorithm and/or a machine learning method besides a DNN may be used.

Figure 2:
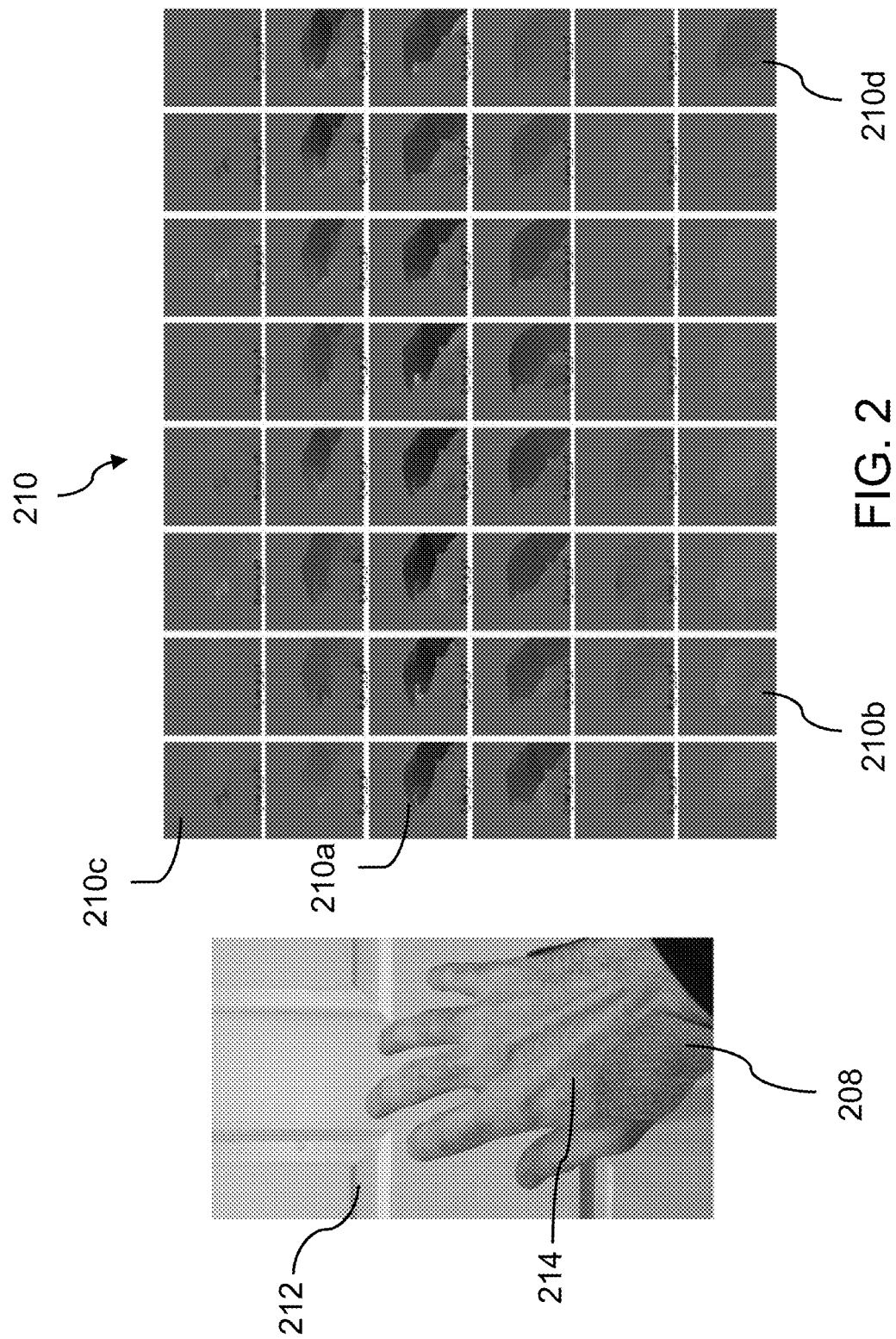
FIG. 2 is a frame of a video and exemplary optical flow images derived from the video

FIG. 2 shows a frame 208 of a video of a hand, along with example optical flows 210 extracted from the same video. Each optical flow (for example, 210a and 210b) includes a pixel map showing an intensity of movement in each location of the frame. For example, because the background features 212 of the frame 208 are static, the background features 212 are not visible in any of the optical flows 210. However, a hand 214 in the frame 208 does move, such that the optical flows 210 shows higher intensities corresponding to the hand (with darker colors indicating a higher intensity of movement).

In some implementations, optical flows may include time-ordered optical flows. For example, from a first optical flow 210c to a last optical flow 210d, a shape corresponding to the hand starts with low intensity, increases in intensity, and then decreases in intensity. The optical flows 210 therefore correspond roughly to a single burst of movement of the hand 208. For example, if the hand 208 is tremoring, then a full set of optical flows extracted from the entire video might show a plurality of such bursts of movement, and a frequency of the bursts (as determined from the full set of optical flows) would correspond to a frequency of the tremor.

Although the optical flows 210 are shown as images, these images are merely representative of optical flow data. In any of the implementations disclosed herein, optical flow images, or other images described in this disclosure (e.g., video frames and/or optical flow maps) may not be directly and explicitly obtained; however, underlying data, of which any images would be a representation, may be obtained and used. For example, underlying data may be in the form of an array or a table, and the underlying data may be used for autoencoder training and biomarker determination as described in this disclosure.

Referring back to the example of FIG. 1, an autoencoder 120 (for example, a trained deep neural network) encodes the optical flows 104 into a feature vector 122 that includes a movement-based biomarker value 124 of the subject (e.g., tremor frequency or movement distance). This encoding, which leads to a determination of the movement-based biomarker value 124, may also be referred to as a "prediction" of the movement-based biomarker value 124.

In any of the implementations disclosed herein, a feature vector may include elements besides a movement-based biomarker value. For example, a feature vector may include a biomarker type. In the example of FIG. 1, the feature vector 122 may include a biomarker type 126. The biomarker type may indicate a specific categorization of the biomarker. For example, in implementations where the video 100 shows a hand tremor, the biomarker type 126 may indicate a particular arrangement of the hand (e.g., hand held in front of body, or hand held under chin). In some implementations, the biomarker type 126 may indicate a specific portion of the subject's body (e.g., a specific limb) corresponding to the movement-based biomarker value 124. For example, the biomarker type 126 may indicate a particular facial muscle group of the subject's face, such that the feature vector 122 stores information about an action unit observed in the subject.

In some implementations, the feature vector may include additional elements. For example, the feature vector 122 may include a plurality of pairs of elements, each pair of elements including a biomarker value and a corresponding biomarker type. The feature vector 122 may include multiple biomarker values corresponding to each biomarker type.

In practice, determination of a feature vector based on optical flows can be a complex process. This is at least because a video (e.g., video 100, from which the optical flows 104 are derived) may be recorded in any one of many conditions (e.g., angles of recording and levels of zoom in the recording) and show any one of many arrangements of the subject (e.g., position and arrangement of the body of the subject, and portion of the body of the subject shown), such that the encoding process performed by the autoencoder is not trivial. Therefore, in any of the implementations disclosed herein, the autoencoder may include, or be trained using, one or more specific features that enable more accurate determination of the feature vector.

At least because optical flows are configured and generated to extract movement features of the video, an autoencoder-based extraction of movement-based biomarker values using optical flows may provide more accurate and/or reliable of movement-based biomarkers values than an autoencoder-based method that does not include optical flows.

In some implementations, as disclosed in further detail below, optical flow maps may be used instead of, or in addition to, optical flows, in order to train an autoencoder and/or or as inputs to an autoencoder resulting in a determined feature vector.

In any of the implementations disclosed herein, an autoencoder (e.g., the autoencoder 120) may be trained using labeled data. Values in the feature vector may be selected in order to improve overall recognition of future images being analyzed, in some implementations being selected based on labels of the labeled data. Because the autoencoder (e.g., autoencoder 120) and the labeled data are categorized to operate in accordance with the values in the feature vector (e.g., feature vector 122), the autoencoder may be able to more easily recognize feature vectors and determine future feature vectors based on future video and/or images.

In any of the implementations disclosed herein, an autoencoder (e.g., autoencoder 330 of FIG. 3) makes use of discrimination and/or reconstruction techniques. When the autoencoder 330 is used to encode optical flows 304 extracted from a video 300 using an optical flow DNN 302, these techniques may provide better accuracy of the determined feature vector 322.

Figure 3:
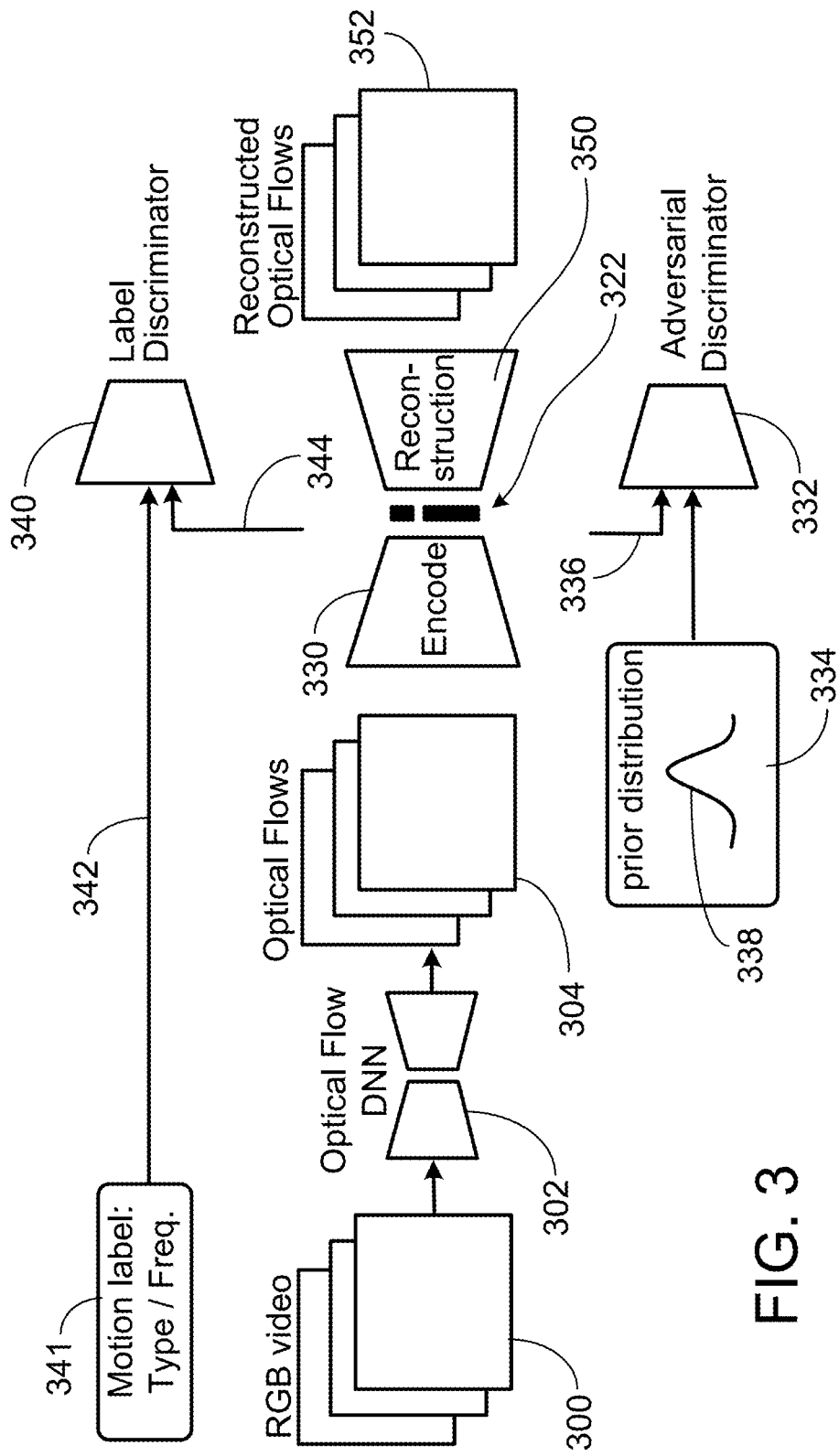
FIG. 3 is a flow chart of an exemplary optical flow adversarial autoencoder

In any of the implementations disclosed herein, an autoencoder may be an adversarial autoencoder based on the use of an adversarial discriminator. For example, as shown in FIG. 3, an autoencoder (e.g., autoencoder 330) is an adversarial autoencoder (e.g., includes adversarial discriminator 332, and/or is trained using adversarial discriminator 332).

The adversarial discriminator 332 receives, as inputs, an output 336 of the autoencoder 330 (e.g., a type or a quantitative characterization of a biomarker, e.g., a frequency of tremors in an output feature vector) and a function 338 output by a prior distribution generator 334. A difference (error) between a distribution of the output 336 and the function 338 (e.g., a distribution represented by the function 338) may be back-propagated into the autoencoder 330 to update parameters of the autoencoder 330, in order to impose structure on an autoencoder space of the autoencoder (e.g., a latent space of the autoencoder) such that generated feature vectors 322 are mapped to the prior distribution. Therefore, an accuracy of determination of the feature vector 322 may be increased compared to a process not making use of an adversarial autoencoder.

In any of the implementations disclosed herein, an autoencoder may include, and/or may be trained using, a label discriminator. For example, as shown in FIG. 3, an autoencoder (e.g., autoencoder 330) is trained using a label discriminator (e.g., label discriminator 340). The label discriminator 340 receives, as input, a data label 342 from a label element 341 and an output 344 of the autoencoder 330. The data label 342 may be, for example, a ground truth label collected during data acquisition (e.g., a known, experimentally-determined value of a frequency of tremors, and/or a known, experimentally-determined type of a motion-based biomarker). A difference (error) between the output 344 of the autoencoder 330 and the data label 342 (corresponding to a particular set of optical flows) may be used to update parameters of the autoencoder 330 via back-propagations (e.g., a gradient descent approach using chain rules), to train the autoencoder to output correct feature vectors 322.

In any of the implementations disclosed herein, a first element of an output feature vector may be used for label discrimination, and a second, different element of an output feature vector may be used for adversarial discrimination. For example, a biomarker type may be used for label discrimination, and a biomarker value may be used for adversarial discrimination. This may improve a resulting accuracy of determined biomarkers.

In any of the implementations disclosed herein, an autoencoder may be trained using a reconstruction network. For example, as shown in FIG. 3, the autoencoder 330 is trained using a reconstruction network, such as reconstruction network 350. The reconstruction network 350 learns to generate reconstructed optical flows 352 based on feature vectors 322 output from the autoencoder 330. For example, for each feature vector 322, the reconstruction network 350 may output reconstructed optical flows 352. The reconstructed optical flows 352 may be compared with the input optical flows 304, and a difference between the two may be back-propagated into the autoencoder 330 and reconstruction network 350 in order to update parameters of the autoencoder 330 and reconstruction network 350. Once the autoencoder 330 and the reconstruction network 350 are trained, the feature vector 322 may be an accurate lower-dimension representation of the input optical flows 304, and the reconstruction network 350 may accurately reconstruct the input optical flows 304.

In some implementations, labeled data (e.g., experimentally-acquired data) may be insufficient for optimal training of the autoencoder 330, and it may be desirable to generate synthetic data for further training. Therefore, in some implementations, a structured autoencoder may be used with the trained reconstruction network in order to synthesize samples for training, e.g., using an adversarial autoencoder image generator, as described below in reference to FIG. 4.

In various implementations, an autoencoder (e.g., the autoencoder 330) may include any type of autoencoder, such as a stacked denoising autoencoder or a variational autoencoder. The autoencoder 330 may include a neural network model (e.g., a DNN model) or another machine learning model, an output of the neural network model and/or machine learning model including determined biomarkers.

Some implementations may include further features to enhance an accuracy of biomarker determination.

For example, in any of the implementations disclosed herein, additional training data (e.g., labeled data used as an input to the label discriminator 340 in FIG. 3) may be used to train the autoencoder, the additional training data having a label similar to, but not the same as, labels of other training data. Weights of the further-trained autoencoder (e.g., autoencoder 330) may then be used to initialize a final movement model of the autoencoder 330. This may increase an accuracy of determined biomarkers by increasing a training range of the autoencoder.

As another example, in any of the implementations disclosed herein, training data used in conjunction with a label discriminator (e.g., label discriminator 340) may be augmented with additional, artificially-created data. For example, real optical flows (e.g., optical flows directly extracted from a video), maps of real optical flows, and/or frames of a video may be randomly processed in order to obtain further optical flows. The random processing may include one or more of random translation, random rotation, random scaling, and random cropping, which may increase a variety of training samples. Additional video frames generated by the random processing may be used to generate additional optical flows. Additional optical flows generated by the random processing, or based on the additional video frames, may be used to train the autoencoder, and/or the additional optical flows may be used to generate additional optical flow maps used for autoencoder training. Additional optical flow maps generated by the random processing, or based on the additional optical flows, may be used for autoencoder training. The use of an augmented training data set (e.g., for use with a label discriminator 340) may increase an accuracy of biomarkers output from the autoencoder, and/or decrease an amount of labeled training data necessary to train the autoencoder.

Figure 4:
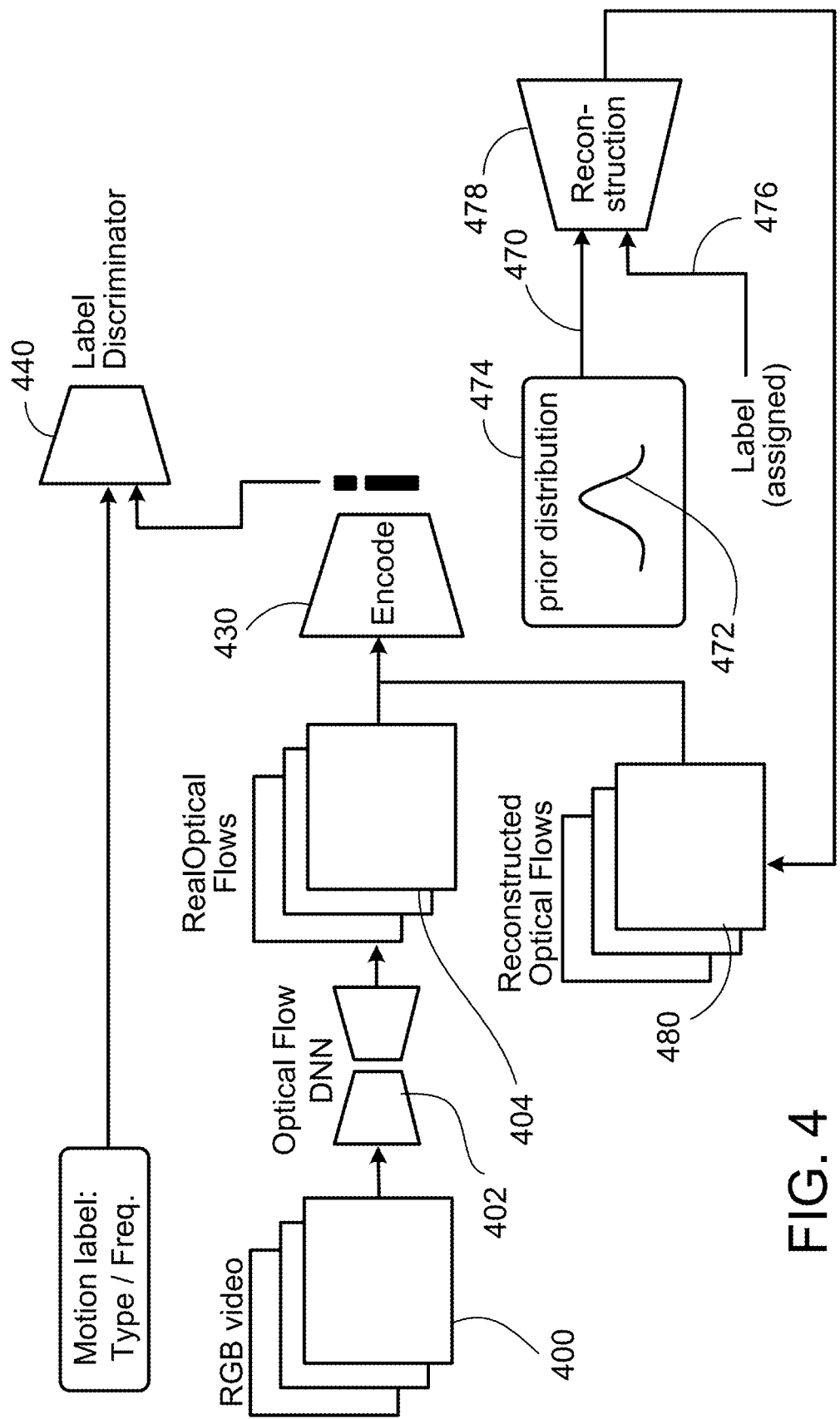
FIG. 4 is a flow chart of an exemplary optical flow autoencoder and an exemplary adversarial autoencoder generator

Any of the implementations disclosed herein may include an adversarial autoencoder image generator. The adversarial autoencoder image generator may use labeled random samples drawn from a distribution used for an adversarial training process to generate reconstructed optical flows for use in autoencoder training. In the example of FIG. 4, real optical flows 404 are extracted from subject video 400 using an optical flow DNN 402. Random samples 470 are drawn from a distribution determined by a function 472 of a prior distribution generator 474 (e.g., a function and a prior distribution generator used to perform adversarial training to map an output of the autoencoder to a distribution defined by the function). The random samples 470 are combined with corresponding labels 476 to generate, by an adversarial autoencoder reconstruction subnetwork 478, reconstructed optical flows 480 having the known label 476, the known label enabling training of the autoencoder 430 using a label discriminator 440, as described above. The label discriminator 440 may use the reconstructed optical flows 480 as further training data in order to update parameters of the autoencoder 430. Therefore, training of the autoencoder 430 may be increased, allowing for more accurate determination of biomarkers.

In any of the implementations described herein, a function (e.g., function 472) used to generate reconstructed optical flows using an adversarial autoencoder reconstruction subnetwork may be a function used in training an autoencoder using an adversarial discriminator. For example, in the implementation of FIG. 3, the function 338 may be used for training using an adversarial discriminator and also used for generating reconstructed optical flows using an adversarial autoencoder subnetwork, as described in reference to FIG. 4. In some implementation, different functions may be used for these processes.

In any of the implementations described herein, an adversarial autoencoder image generator may be trained using an adversarial discrimination process, as described in reference to FIG. 3. In some implementations, an adversarial discrimination process may be used to impose structure on an autoencoder space of an autoencoder and also used to train an adversarial autoencoder image generator. In some implementations, an image generator different from the adversarial autoencoder image generator, trained using adversarial discrimination, may be used.

In any of the implementations described herein, a reconstruction network (e.g., reconstruction network 350) may include an adversarial autoencoder reconstruction subnetwork, and the reconstruction network may perform the reconstructed optical flow generation described in reference to the adversarial autoencoder reconstruction subnetwork 478.

The implementation of FIG. 4 also includes a label discriminator 440, as described in reference to FIG. 3. The adversarial autoencoder image generation shown in FIG. 4 may be combined with any or all of the elements described in reference to FIGS. 1 and 3. Features described in reference to any implementation of FIGS. 1, 3, and 4 may be combined with or used in conjunction with features of another implementation of FIGS. 1, 3, and 4. In addition, the processes shown in any of FIGS. 1, 3, and 4 may be modified to include other features described in this disclosure.

In some implementations, in order to encode video into feature vectors describing biomarker values and/or types, movement labels are used in order to force biomarker type and/or biomarker value separation in model training. Such implementations may include one of labeling movement by a biomarker value (e.g., tremor frequency), labeling movement by a biomarker type (e.g., a hand position), or labeling movement by both a biomarker value and a biomarker type.

In some implementations, collected data is labeled with a biomarker value but not a biomarker type. However, an autoencoder trained on this collected data may predict not only biomarker value but also biomarker type (a latent variable). In some implementations, the autoencoder assumes that, in the training data (e.g., a population of images and/or video used to the train the autoencoder), movement can be decomposed into a biomarker value and a biomarker type, and that movement can be completely represented by the biomarker value and the biomarker type. That is, although the autoencoder may train on only the biomarker value, a remaining element besides the biomarker value out of two elements in an output feature vector implicitly represents biomarker type. Therefore, once trained, the autoencoder may predict, for example, not only movement frequency but also movement type, even though movement type labels may not be available as a ground truth in the training data (e.g., experimental data).

In some implementations, collected data is labeled with a biomarker type but not a biomarker value. In such implementations, implicit training for the latent variable can be performed (as described above for the biomarker type), such that the trained autoencoder may predict, for example, not only movement type but also movement frequency, even though movement frequency labels may not be available as a ground truth in the training data.

In some implementations, collected data is labeled with a biomarker type and with a biomarker value. The autoencoder may be trained using both labels, resulting, in some implementations, in a stronger separation between biomarker type and biomarker value due to the supervised learning process with more complete information incorporated.

In some implementations, an autoencoder may determine three or more values and be trained using data labeled with fewer values than the three or more values.

As described above, encoding of movement using optical flows has many practical applications. In clinical and other medical research areas, determination of movement biomarkers based on subject video may be valuable for predicting and/or recognizing movement for the purposes of confirming medication adherence, and for detecting any suspicious, undesirable, or unexpected movement of an individual during a medication administration process. Encoding using optical flows may be used to determine relative motion of the hand or other body part of the subject when the subject is performing one or more predetermined motions, exercises, tasks, or other expected movements. Such motions, exercises, or tasks may be performed as part of another action, or specifically in response to a request to the subject to perform a specific action. Such a request may be presented to the subject on the display of a mobile device or may be part of an action typically performed by the individual, either with prompting or as performed by the individual in a normal course of activity. For example, an application on a mobile phone may prompt the subject to perform an action, and a camera of the mobile phone may subsequently record a video of the action. One or more processors located on the mobile phone and/or at a remote server may then perform the processes disclosed herein.

Processes disclosed herein may be applied to the monitoring of tremors. In such an implementation, a feature vector may include a movement frequency that can be directly used for clinical diagnosis. The frequency of movement can be correlated to actual tremor, and the actual tremor in turn correlated to diagnosis, monitoring, and monitoring of progression of disease. The frequency of movement may be used to evaluate the condition of a subject in a vegetative state.

In some implementations, the processes disclosed herein may be applied to action unit and expression determination. In such an implementation, action units may be based on facial muscle groups, and a feature vector may include 2 or more elements. A first element may be a biomarker type to represent different muscle groups. A second element may be a biomarker value giving a measure of movement frequency. In some implementations, a third element of the feature vector may be a biomarker value representative of movement intensity. In some implementations, the feature vector may include an expression label.

A movement framework according to an action unit and expression determination implementation may be used to predict action units instead of, or in addition to, using a landmark-based action unit identification method (e.g., OpenFace). Implementations as described herein may allow for a higher level of analysis and/or further allow for more direct and precise monitoring of changes in facial action units, which in turn may be more indicative of expression changes or changes in other attributes of a subject.

Implementations for determining action units may include action unit labeling. However, in some implementations, manual labeling of action units or muscle groups, such as when labeling units in the face of a video subject, may be labor-intensive and subject to observer errors and inconsistency.

Therefore, implementations employing features disclosed herein (e.g., features described in reference to FIGS. 1, 3, and/or 4) may also be used in conjunction with labeled action unit label data collected using an electric stimulator. Electrodes may be placed on subject faces at locations of different muscle groups, and the frequency and intensity of stimulation delivered to the electrodes may be controlled in order to induce different facial movements while recording videos. The frequency and intensity of the facial movements correspond to the frequency and intensity of stimulation. Therefore, a known "ground truth" for the facial movements may be generated, the known ground truth labels being used for training the autoencoder (e.g., using a label discriminator as described above). Data labeled in this manner may be more useful (e.g., for training an autoencoder) than data labeled by raters or by other methods.

An electrode stimulation process may be employed with other muscles in the body, e.g., by placing electrodes on the hands of a subject.

Some implementations using optical flows to derive biomarkers may be applied to medication adherence determination. A video may record a subject taking medication, and biomarkers may be extracted from optical flows of the video (using an autoencoder as described above) in order to determine biomarkers including movement type and movement frequency. The autoencoder may determine whether the subject successfully or truly administered the medicine.

In some implementations, medication adherence determination videos, or other videos, may be used for disease-specific processes. For example, videos of subject having known diseases may be used for training (with a disease-indicating label), and a feature vector may include a biomarker type indicating a disease of the subject. Videos may be clustered by different patient diseases to build a prediction model for an autoencoder. In some implementations, therefore, the autoencoder may predict (determine) a disease of a subject.

In order to provide further details and examples of optical flows used in conjunction with an autoencoder to determine biomarkers, an experimental example is now disclosed.

A model was first trained on collected volunteer data, and was then further evaluated employing patient videos (data collected from individuals using a medication adherence monitoring system). The patient videos were collected at a variety of focus levels. Collected patient videos were first scored by raters from 0 to 4 based on a distance of finger movement in the videos. However, due, in some implementations, to lack of means to estimate distance from videos, such rater-based tremor scoring may be subject to intra- and inter-observation variability.

The volunteer data was labeled with accurate movement frequency labels. Tremors were produced by using an electronic pulse massager to deliver electrical stimulus to one of each volunteer's hands via two 2×2 inch electrodes. The pulse massager allowed for applying controlled stimuli at regular intervals to the hand to recreate the amplitude and frequency of a clinical tremor. One electrode was placed on each side of the hand, as localized as possible to the abductor pollicis brevis and between the first and second dorsal interrossei muscles. The median nerve branch of the brachial plexus, which controls coarse movements of the hand, was targeted for stimulus to recreate the appearance of tremor. The frequency and amplitude of the applied stimuli were used as the frequency and amplitude labels for training an autoencoder.

42 videos from 23 volunteers were recorded with a hand forward pose at three different stimulus frequencies each, the stimulus frequencies being 0 Hz (no stimulation), 4 Hz, 10 Hz, using the volunteer data acquisition protocol, as described above. These frequencies were chosen based on commonly-observed clinical tremor frequencies. Each video lasted approximately 15 seconds and was divided into multiple overlapping video clips at 0.5 second intervals, each clip having a length of 2 seconds. In total, 6696 video clips were prepared in this manner. The length of video clips (2 seconds) was determined to cover sufficient hand movements for tremor quantification. Because of the discrepancy in subject responses to electronic stimuli, the videos were first manually reviewed, and the videos in which no induced tremors were observed were excluded. Then, optical flow maps derived from frames of the remaining videos were down-sampled to 64×64 pixels each in width and height to lower computational cost.

Although this experimental example uses stimulated hand tremors, data labeled based on direct stimulation or on direct measurement (e.g., using sensing electrodes applied to the body of a volunteer) may be used in combination with any of the implementations disclosed herein. Labeled data obtained in this manner (as opposed to, e.g., data labeled by a rater) may enhance an accuracy of a trained autoencoder by providing more accurate and reliable training data.

In any of the implementations disclosed herein, optical flows may be processed into optical flow maps that include information derived from two or more optical flows. For example, an optical flow map may include movement data extracted from a video at multiple time-points or across multiple pairs of frames. At least because optical flow maps may include data of multiple individual optical flows, optical flow maps may be used in place of, or in addition to, optical flows with respect to any of the features disclosed herein. For example, an autoencoder may be trained to output feature vectors based on one or more input optical flow maps. As another example, an autoencoder may be trained using labeled optical flow maps in conjunction with a label discriminator. As another example, a reconstruction network or an adversarial autoencoder image generator may output reconstructed optical flow maps for use in training an autoencoder (e.g., with a discriminator, e.g., a label discriminator). Because underlying data may be represented in either optical flow form or optical flow map form, either or both forms may be used in any of the implementations described herein.

Figure 5:
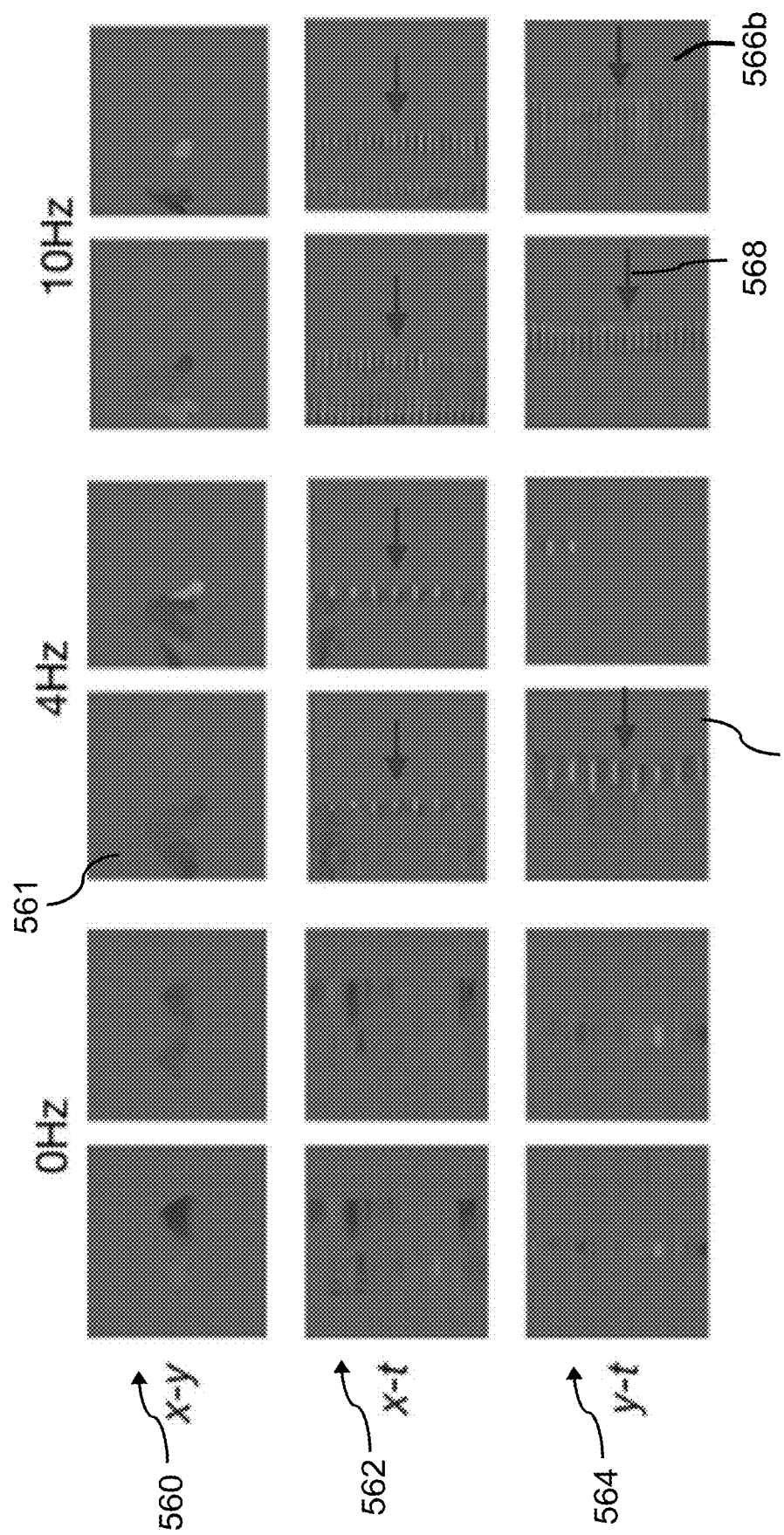
FIG. 5 is an exemplary output from optical flow processing

FIG. 5 shows examples of data, including example optical flows and optical flow maps, resulting from the volunteer studies described above. The first row 560 shows single optical flows (e.g., optical flow 561) of the subjects for each applied stimulus frequency. These individual optical flows do not show patterns of movement.

In any of the implementations disclosed herein, optical flow maps may include a representation of optical flow data that has been reduced in dimensionality. For example, optical flow maps may be generated using a cutting and/or an averaging across one dimension of a multi-dimensional dataset of multiple optical flows, in order to reduce an amount of data included in the optical flow maps, e.g., in order to make the optical flow maps more easily understood, and/or in order to decrease an amount of optical flow map data that must be processed (e.g., by an autoencoder).

For example, in the example of FIG. 5, the second and third rows 562, 564 each show, for each of the three applied stimulus frequencies, two example optical flow maps (e.g., optical flow maps 566a and 566b), the example optical flow maps showing an intensity of movement along a spatial cut of each optical flow extracted from a given video (for row 562, ay-cut; for row 564, an x-cut). A three-dimensional x-y-t dataset has been cut in order to produce the two-dimensional optical flow maps of rows 562, 564.

A horizontal axis of each optical flow map represents a spatial position along the respective cut (an x value for row 562 and ay value for row 564), and a vertical axis of each optical flow map represents a time. A color of each pixel of the example optical flow maps indicates an intensity of movement at the given x-t coordinate or y-t coordinate, as determined in a corresponding optical flow.

Optical flows in the "0 Hz" column (corresponding to videos where no stimulus was applied) show no particular patterns. However, optical flows in the "4 Hz" and "10 Hz" columns (corresponding to videos in which those stimulus frequencies were applied) show stripe patterns (indicated by dark gray arrows, e.g., arrow 568) indicative of tremor. The cyclical appearance of these patterns in the t direction indicates a frequency of the tremor, while the localized appearance of these patterns in the x- or y-direction indicates that the tremor is localized in a particular portion of each video frame. Because optical flow map 566b was extracted from a video in which the stimulation frequency was higher than for optical flow map 566a, the stripes in optical flow map 566b have a higher frequency of cycle in the t-direction than the stripes in optical flow map 566a.

After optical flow extraction of the dynamic information from the volunteer tremor videos, a three-way deep neural network classifier autoencoder learned to determine tremor frequency (determine whether movement had a frequency of 0 Hz, 4 Hz, or 10 Hz) based on the extracted optical flows. The autoencoder was then supplemented with three further features.

Although this example uses three stimulation frequencies of 0 Hz (no stimulation applied), 4 Hz, and 10 Hz, in other implementations other stimulation frequencies and/or more stimulation frequencies may be applied. In some implementations, experimentally-obtained data may include data labeled with many stimulation frequencies (or another biomarker value), and an autoencoder may be trained to determine a frequency value over a continuous range rather than, or in addition to, classifying between three discrete, pre-selected values.

As a first supplement, using the same image acquisition system as described above, another volunteer (who was not among the 23 volunteers from whom the validation data was acquired), was also video recorded employing the hand forward pose at three other frequencies: 0.99 Hz, 3.98 Hz, and 9.96 Hz, each video lasting 30 seconds. The autoencoder was trained based on this dataset, and the trained weights of the autoencoder were used to initialize a final movement model for training using data of the 23 volunteers, as described above in reference to FIG. 3.

As a second supplement, original optical flow maps were processed with random translation, rotation, scaling, and cropping to increase the variety of training samples. These random processes may simulate real-world variety in video recording conditions. Optical flow maps resulting from this processing were added to the training data to augment the training set at every other iteration, as described above in reference to FIG. 3. In some implementations, random processing to augment a training set may be performed every iteration, or at another rate different from every other iteration.

As a third supplement, the autoencoder was trained using an adversarial autoencoder image generator, as described above in reference to FIG. 4. A same number of random samples as had been used for the original training samples were drawn from a prior distribution after the adversarial autoencoder network was optimized. These random samples were passed to an adversarial autoencoder subnetwork as seed latent vector. Reconstructed optical flows and/or optical flow maps were generated by the adversarial autoencoder subnetwork were pooled together with the experimentally-collected samples and the augmenting randomly-generated optical flows of the second supplement in order to increase the total training sample for autoencoder training.

Due at least to the limited number of subjects available for data acquisition, leave-one-out cross-validation method was used to evaluate trained autoencoders. Eight testing subjects were selected from the original 23 subjects for validation. These testing subjects were based upon a determination of a sufficient length of induced tremors recorded in their videos. Eight different models were trained (with four versions each, as described below), corresponding to the eight testing subjects. First, an adversarial autoencoder was trained excluding data from all eight testing subjects; then, an individual autoencoder (classifier) subnetwork was trained for each testing subject.

Figure 6:
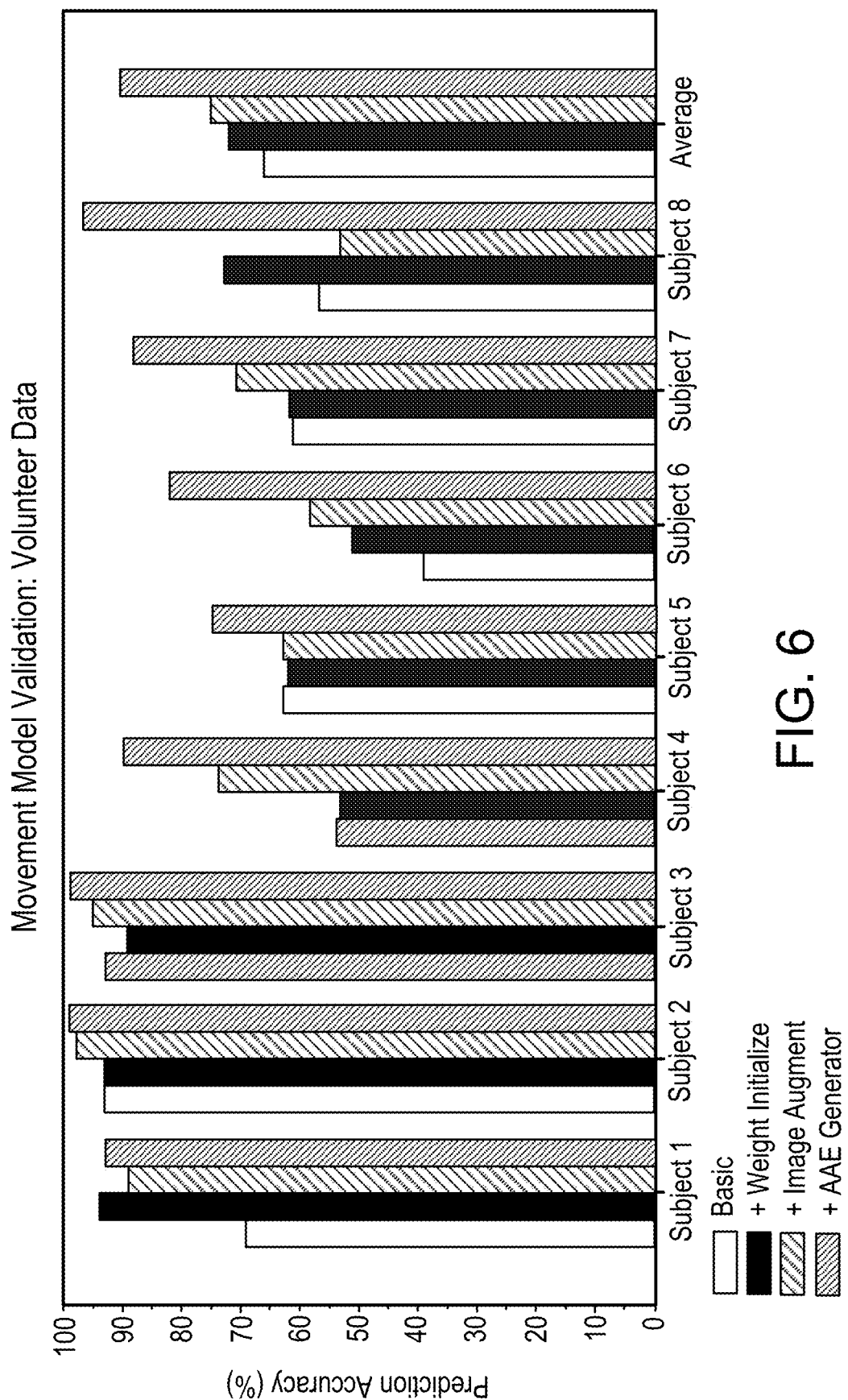
FIG. 6 is a histogram of exemplary prediction accuracies

FIG. 6 depicts example evaluations of prediction accuracy (i.e., determination of biomarkers) for the eight testing subjects using four different methods: a basic three-way classifier to choose between 0 Hz, 4 Hz, and 10 Hz for a determined movement frequency (legend "Basic" in FIG. 6), the basic three-way classifier having the features shown in FIG. 3; the basic three-way classifier supplemented with weight initialization (legend "+Weight Initialize" in FIG. 6); the basic three-way classifier supplemented with weight initialization and image augmentation (legend "+Image Augment" in FIG. 6); and the basic three-way classifier supplemented with weight initialization, image augmentation, and adversarial autoencoder image generation (legend "+AAE Generator" in FIG. 6). The right-most bar group in FIG. 6 is the average accuracy of all the testing subjects. The accuracy of FIG. 6 is derived from a comparison of movement frequency as determined by an autoencoder (i.e., a biomarker value and/or biomarker type of a feature vector output by an autoencoder) as compared to the experimentally known movement frequencies imposed by the stimuli.

As is shown in FIG. 6, model weight initialization with a similar data set may stabilize an autoencoder optimization process and thereby increased biomarker determination accuracy. Image augmentation may also increase determination accuracy by adding variety to training data. Adversarial autoencoder image generation may also boost prediction accuracy, in some implementations by compensating for a relatively small amount of data used for autoencoder training.

As a further evaluation of movement-based biomarker determination based on optical flow analysis, an autoencoder was trained by data from 33 clinical videos collected from nine essential tremor patients. Each of the clinical videos was rated by a rater, with scoring from 0 to 4 determined by a distance of tremor movement. TABLE 1 shows a specific set of labeling criteria.

Figure 7:
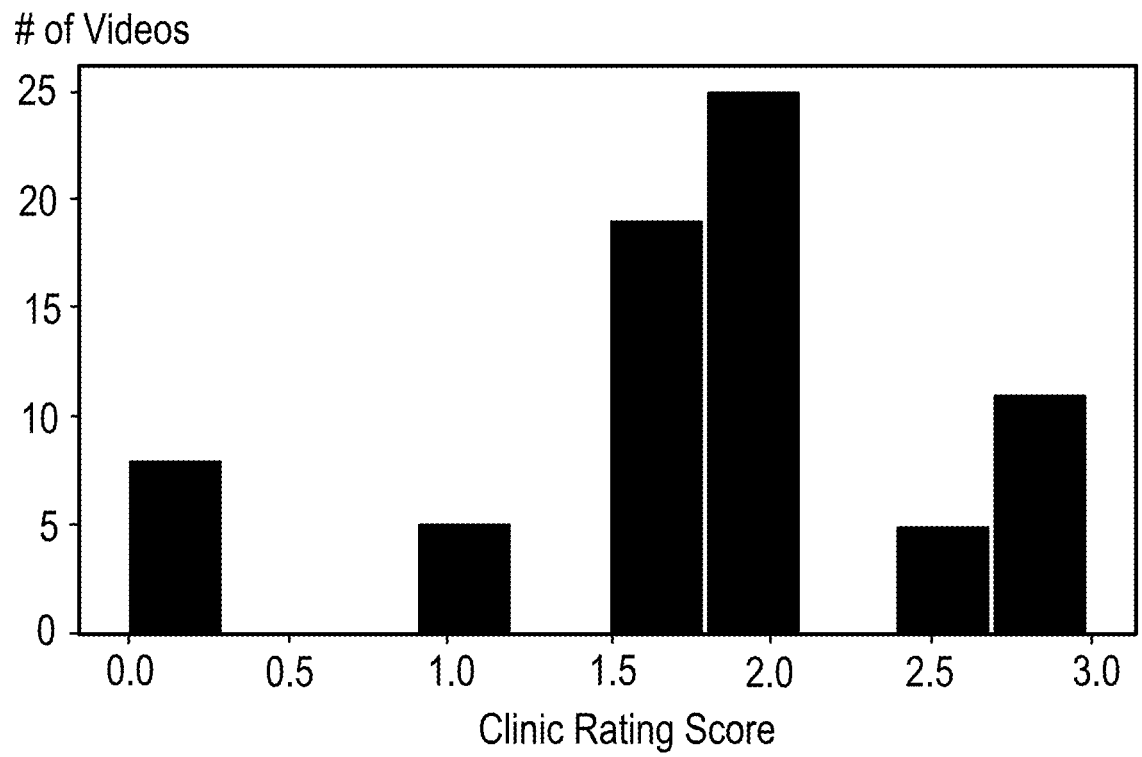
FIG. 7 is a histogram of exemplary clinical rating scores

Video segments showing left or right hand forward poses were extracted for movement model evaluation. FIG. 7 depicts the histogram of the clinical scores (scores determined by raters) for the extracted video segments.

TABLE 1

| Hand | 0 | 1 | 1.5 | 2 | 2.5 | 3 | 3.5 | 4 | Score |
|---|---|---|---|---|---|---|---|---|---|
| R-forward | none | barely visible | <1 cm | 1-<3 cm | 3-<5 cm | 5-<10 cm | 10-20 cm | >20 cm | 2 |
| L-forward | none | barely visible | <1 cm | 1-<3 cm | 3-<5 cm | 5-<10 cm | 10-20 cm | >20 cm | 1.5 |

The extracted video segments with left or right hand forward poses were also divided into multiple overlapping video clips at 0.5 second intervals, each clip having a length of 2 seconds. The original clinical video segments were recorded at six different sites with different devices and resolutions. To eliminate this device difference, the original video segments were cropped to match the size of the volunteer videos described above, and the original video segments were also down-sampled to the same 64×64 resolution as the volunteer videos.

Tremor in the clinical videos was rated by movement distance in centimeters, as described above. However, in some cases, it may be difficult for even a trained expert to estimate an absolute movement distance from videos in a consistent way among different observations, or for different raters to agree on a rating for a given observation. Taking into consideration this intra- and inter-rater variability and the lack of ground truth, the evaluation of clinical data did not focus on absolute accuracy. Instead, the evaluation targeted correlation between the clinical rating scores and the determined biomarkers of an autoencoder model.

Figure 8:
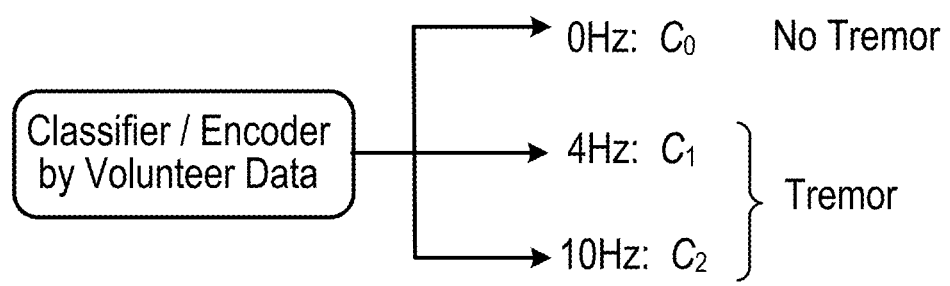
FIG. 8 is a flowchart of frequency outputs from an exemplary trained classifier to prediction probabilities

While the output of the three-way classifier from the trained autoencoder model is a categorical movement frequency (0 Hz, 4 Hz, and 10 Hz), clinical scores indicate tremor severity. Therefore, as shown in FIG. 8, instead of directly using categorical frequency outputs from the trained autoencoder, continuous values from a last layer of a DNN of the autoencoder were used as the prediction probability of tremor in videos, using the equation $P_{tremor}=1-c_2-c_3$.

Figure 9:
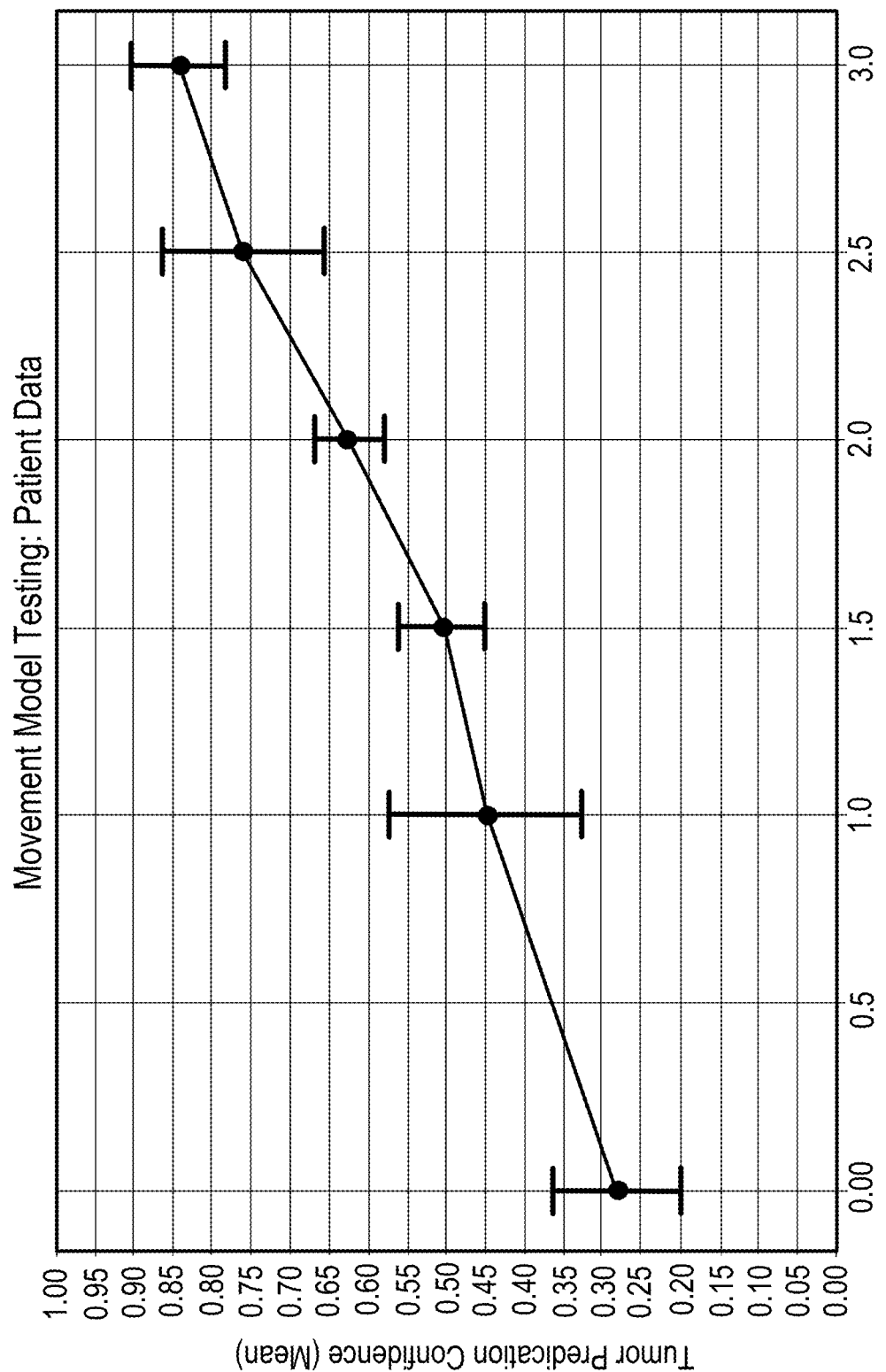
FIG. 9 is a line graph of a correlation of a clinical rating of tremor and a prediction probability of tremor from an exemplary model

FIG. 9 shows mean prediction probability of tremor plotted against clinical rating score of tremor severity for the clinical videos. Error bars in the plot are 95% confidence intervals of the mean, using a t-distribution. The prediction probability of tremor from the autoencoder is highly correlated with the clinical rating score of tremor severity (Pearson's correlation coefficient r=0.99). These results may indicate that the autoencoder is more confident in determining tremor-related biomarkers when a human rater indicates more severe tremor, whereas the model is less confident when a human rater indicates milder tremor (e.g., less visually-noticeable tremor).

As shown in FIG. 9, autoencoder determinations of "no tremor" are less accurate than "tremor" determinations. One reason for this difference in performance (in this particular example) may be that training data was collected from healthy volunteers who were able to hold their hands very steady, almost motionless in many recorded videos, whereas the patients in the clinical videos may have had difficulty holding their hands steady even without an underlying tremor condition, due to their ages or underlying health conditions. That is, even in clinical videos with tremor rating 0, unintentional hand motion may be observed more often than is observed in healthy volunteers.

The validation results shown in FIG. 9 demonstrate that a movement-based biomarker model using optical flows, trained by labeled volunteer data (e.g., volunteer data obtained experimentally as described above), can, in some implementations, be used as an instrument for consistent, reproducible, and objective tremor quantification. In some implementations, validation results may differ from those shown in FIG. 9, which are drawn from a single, merely exemplary study.

Figure 10:
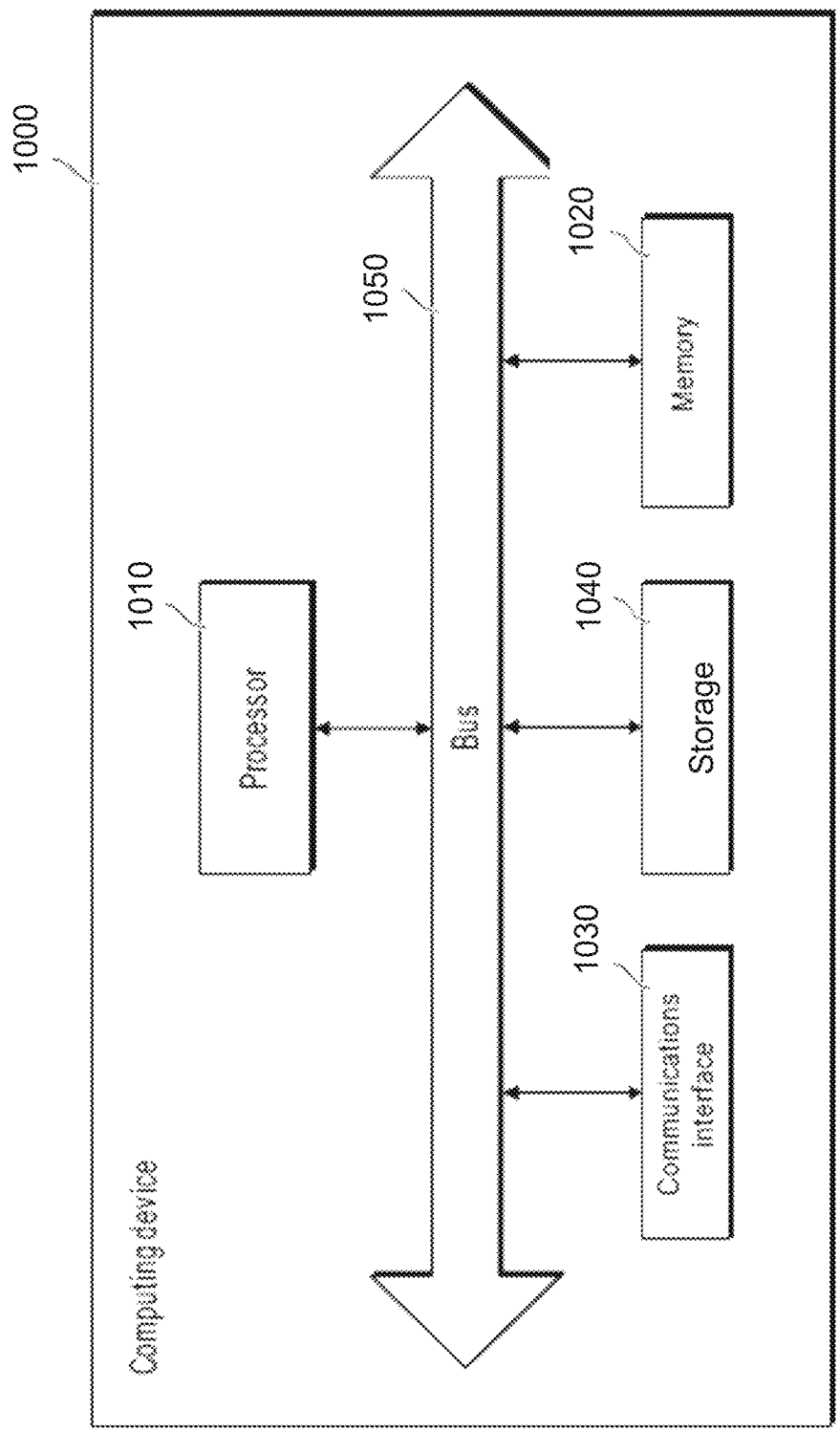
FIG. 10 is a schematic of an exemplary computer system.

In some implementations, methods and features described above may be implemented by one or more computing devices. As shown in FIG. 10, a computing device 1000 may include at least one or more of: one or more processors 1010, one or more memories 1020, one or more communications interfaces 1030, one or more storage devices 1040, and one or more interconnecting buses 1050.

Figure 11:
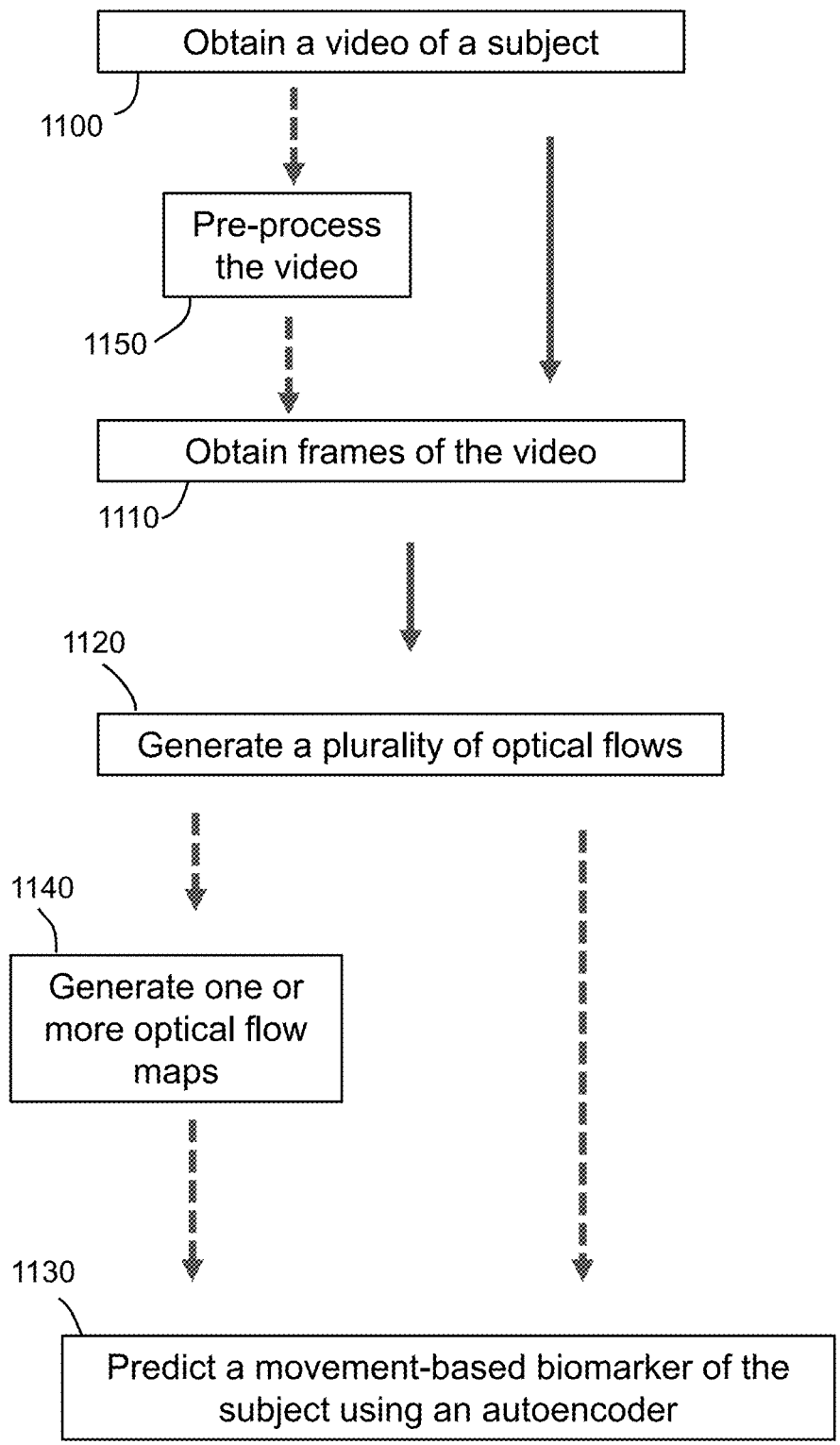
FIG. 11 is a flow chart of an exemplary biomarker prediction process.

As shown in FIG. 11, implementations as described herein may perform operations including: obtaining a video of a subject 1100, obtaining frames of the video 1110, generating a plurality of optical flows 1120, and predicting a movement-based biomarker of the subject 1130. In some implementations, the predicting is based on the plurality of optical flows. In some implementations, the predicting is based on one or more optical flow maps generated (1140) based on the plurality of optical flows. In some implementations, the video is pre-processed (1150). FIG. 1 shows an example of a system and process according to FIG. 11. Dashed lines in FIG. 11 indicate steps flows that may be optional in some optical flow generation processes (and/or movement-based biomarker determination processes) based on a video of a subject.

Figure 12:
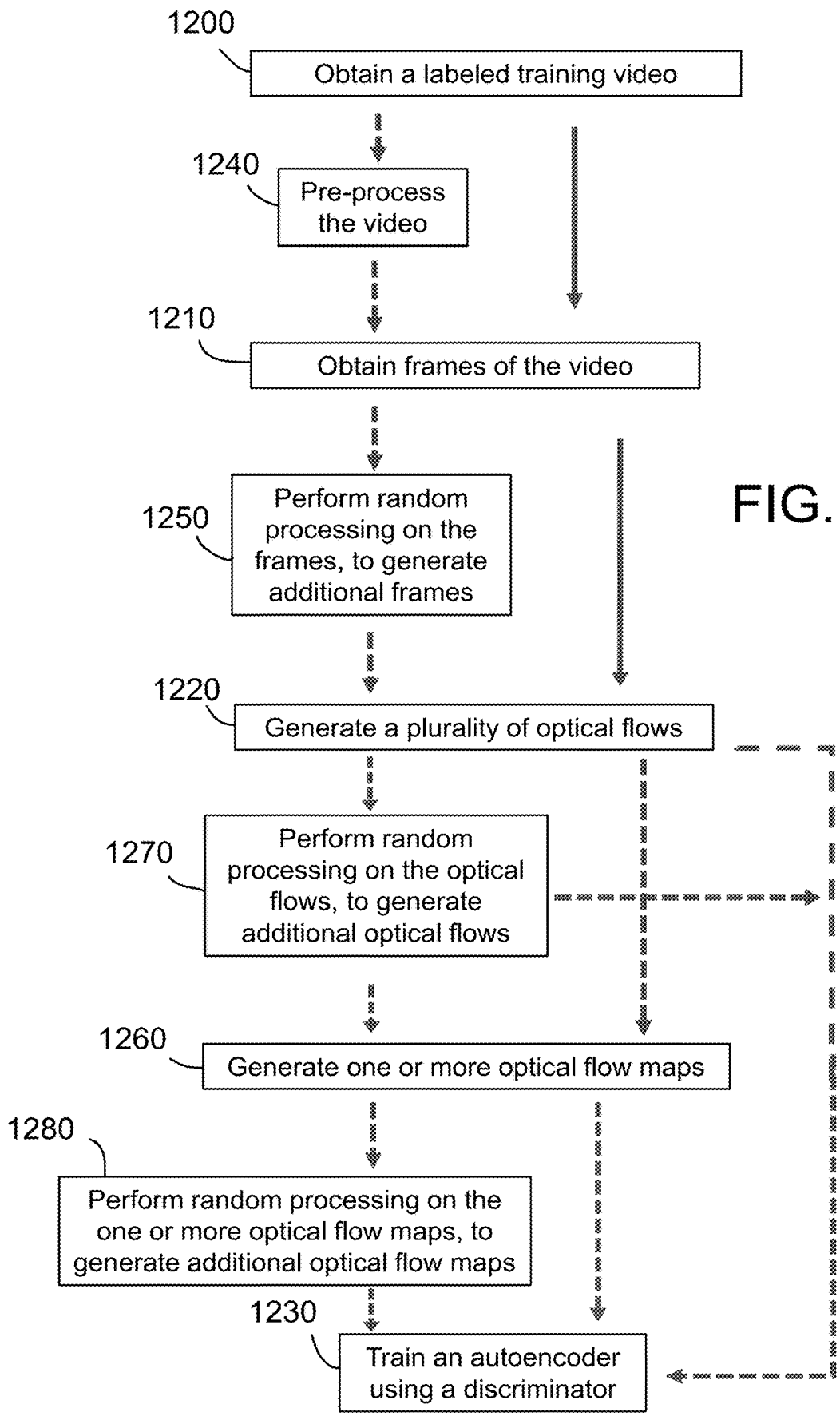
FIG. 12 is a flow chart of an exemplary autoencoder training process.

As shown in FIG. 12, implementations as described herein may perform operations including: obtaining a labeled training video 1200, obtaining frames of the video 1210, generating a plurality of optical flows 1220, and training an autoencoder using a discriminator (1230), the autoencoder being trained to determine biomarkers. In some implementations, the labeled training video is preprocessed (1240). In some implementations, random processing is performed on the frames, to generate additional frames 1250 (on which the plurality of optical may, in some implementations, be based). In some implementations, one or more optical flow maps are generated (1260) based on the generated plurality of optical flows and/or based on additional optical flows generated by performing random processing on the generated plurality of optical flows (1270). In some implementations, random processing is performed on the one or more optical flow maps, to generate one or more additional optical flow maps (1280). In some implementations, the autoencoder may be trained based on the optical flow maps (e.g., using a discriminator). Dashed lines in FIG. 12 indicate step flows that may be optional in some training implementations based on a labeled training video.

As described above and in reference to FIG. 13, in some implementations, other training methods and/or additional training methods (including, for example, pre-processing of training video data) may be used.

FIGS. 3 and 4 each show examples of systems and processes according to FIGS. 11 and 12. FIG. 11 shows an example process including "predict a movement-based biomarker," and FIG. 12 shows an example process including "train an autoencoder using a discriminator." FIGS. 3 and 4 each incorporate aspects of both of these processes. Features of implementations according to FIGS. 1, 3, 4, 11, 12, and 13 may be combined, even if the features are not explicitly shown in a single implementation.

Figure 13:
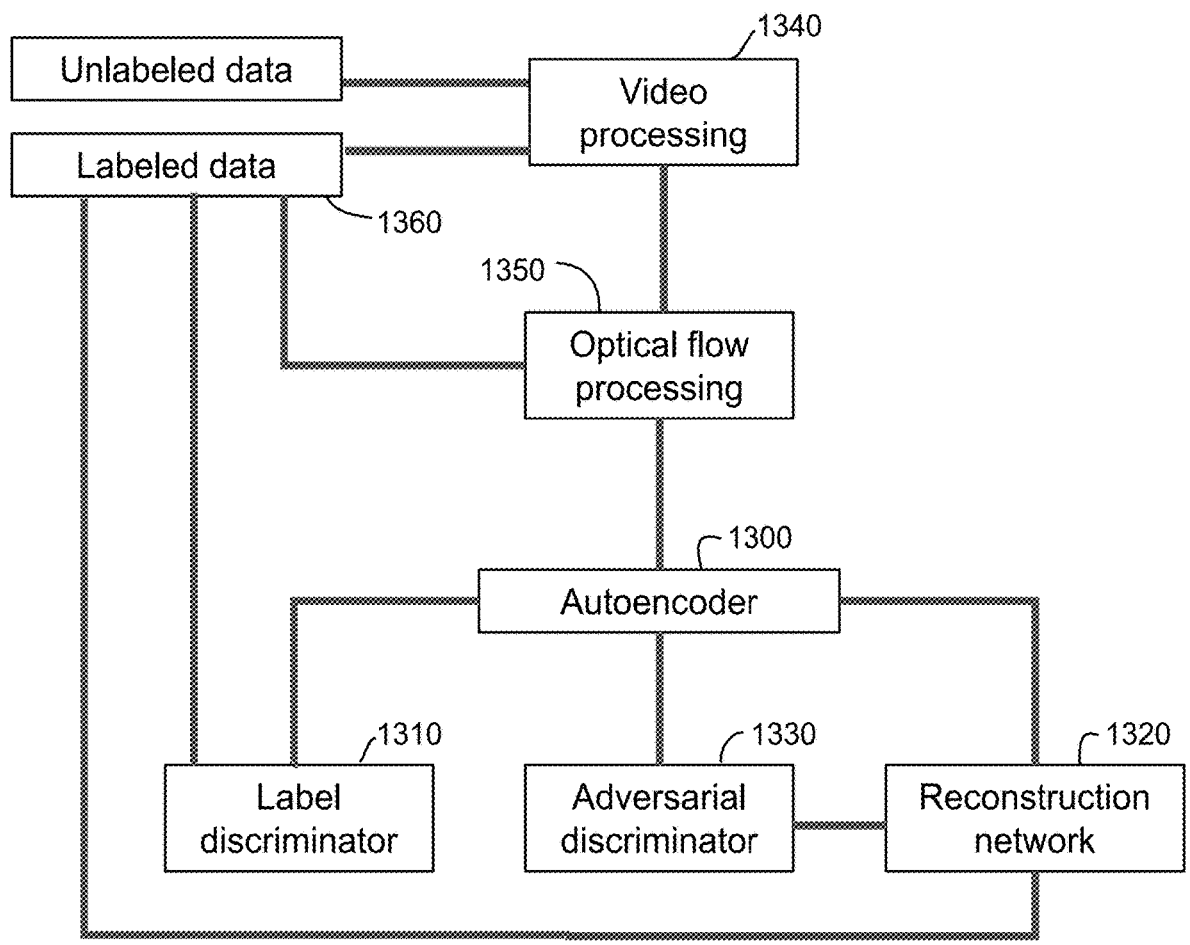
FIG. 13 is a block diagram of an exemplary autoencoder system.

All or a portion of the features described above (e.g., discriminators, encoders, and networks) may be implemented as computational modules. For example, in one example, as shown in FIG. 13, modules may include one or more of: an autoencoder module 1300 that determines one or more biomarkers (e.g., biomarker values and/or biomarker types) based on input data; a label discrimination module 1310 that receives output from the autoencoder and performs discrimination training of the autoencoder based on differences between the output from the autoencoder and labeled data (e.g., experimentally-obtained labeled data, labeled data generated by random processing, and/or reconstructed data based on an autoencoder output and a reconstruction network module 1320 operating, for example within or as part of an adversarial autoencoder generator); the reconstruction network module 1320, which may return reconstructed optical flows and/or reconstructed optical flow maps to the autoencoder module for training; an adversarial discrimination module 1330 that trains the autoencoder, e.g., based on a comparison of an autoencoder output to a distribution; a video processing module 1340 that performs operations (e.g., standardizing, filtering, and frame extraction) on input data; an optical flow processing module 1350, which may extract or process optical flows and/or optical flow maps in accordance with the implementations disclosed herein, and provide input to the autoencoder 1300; and a labeled data processing module 1360, which may provide labeled data to the label discriminator module 1310, receive data from the reconstruction network 1320 for distribution, and/or generate augmented data (e.g., randomly-processed optical flows and/or optical flow maps). Details on the operations of each of these modules are given elsewhere in this disclosure.

Implementations as described herein may not include each module shown in FIG. 13. For example, in some implementations, an optical flow processing module may receive video data directly, without a video processing module. As another example, in some implementations, one or more of the label discrimination module, the adversarial discrimination module, and the reconstruction network module may be removed, and such a system may still be operable to determine movement-based biomarkers as disclosed herein. Implementations are not limited to these examples. In addition, although connection lines in the example of FIG. 13 are depicted as solid, some described connection between modules may not be included in every implementation (e.g., are optional), and additional connections not depicted in FIG. 13 may be included in some implementations, in accordance with the implementations described herein.

Modules may be implemented as individual software programs, combined with other modules in software, and/or implemented fully or partially (in some implementations, combined with other modules) as discrete physical components Therefore, in accordance with the various embodiments of the disclosure, improved methods and systems are provided for determining movement-based biomarkers based on optical flow analysis by an autoencoder.

All or part of the processes described herein and their various modifications (hereinafter referred to as "the processes") can be implemented, at least in part, via a computer program product, i.e., a computer program tangibly embodied in one or more tangible, physical hardware storage devices that are computer and/or machine-readable storage devices for execution by, or to control the operation of, data processing apparatus, e.g., a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a network.

Actions associated with implementing the processes can be performed by one or more programmable processors executing one or more computer programs to perform the functions of the calibration process. All or part of the processes can be implemented as, special purpose logic circuitry, e.g., an FPGA (field programmable gate array) and/or an ASIC (application-specific integrated circuit). Other embedded systems may be employed, such as NVidia® Jetson series or the like.

Processors suitable for the execution of a computer program include, by way of example, both general and special purpose microprocessors, and any one or more processors of any kind of digital computer. Generally, a processor will receive instructions and data from a read-only storage area or a random access storage area or both. Elements of a computer (including a server) include one or more processors for executing instructions and one or more storage area devices for storing instructions and data. Generally, a computer will also include, or be operatively coupled to receive data from, or transfer data to, or both, one or more machine-readable storage media, such as mass storage devices for storing data, e.g., magnetic, magneto-optical disks, or optical disks. Processors "configured" to perform one or more of the processes, algorithms, functions, and/or steps disclosed herein include one or more general or special purpose processors as described herein as well as one or more computer and/or machine-readable storage devices on which computer programs for performing the processes are stored.

Tangible, physical hardware storage devices that are suitable for embodying computer program instructions and data include all forms of non-volatile storage, including by way of example, semiconductor storage area devices, e.g., EPROM, EEPROM, and flash storage area devices; magnetic disks, e.g., internal hard disks or removable disks; magneto-optical disks; and CD-ROM and DVD-ROM disks and volatile computer memory, e.g., RAM such as static and dynamic RAM, as well as erasable memory, e.g., flash memory.

Components may be coupled (e.g., communicably coupled) over one or more networks or physically within a device. Coupling may include the capability to transmit data, including instructions, back and forth between the components.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the user device, which acts as a client. Data generated at the user device, e.g., a result of the user interaction, can be received from the user device at the server.

Other implementations not specifically described herein are also within the scope of the following claims. Logic flows depicted in the figures do not require the particular order shown, or sequential order, to achieve desirable results. In addition, other actions may be provided, or actions may be eliminated, from the described flows, and other components may be added to, or removed from, the described systems. Likewise, actions depicted in the figures may be performed by different entities or consolidated. Furthermore, various separate elements may be combined into one or more individual elements to perform the functions described herein. In some cases, multitasking and parallel processing may be advantageous.

While visual signals are mainly described in this invention, other data collection techniques may be employed, such as thermal cues or other wavelength analysis of the face or other portions of the body of the user. These alternative data collection techniques may, for example, reveal other movement-based biomarkers of the patient, such as changes in blood flow, etc. Additionally, visual depth signal measurements, combined with the use of optical flows, may allow for capture subtle facial surface movement correlated with the symptom that may be difficult to detect with typical color images.

It should be noted that any of the above-noted inventions may be provided in combination or individually. Elements of different embodiments described herein may be combined to form other embodiments not specifically set forth above. Elements may be left out of the processes, computer programs, etc. described herein without adversely affecting their operation. Furthermore, the system may be employed in mobile devices, computing devices, cloud based storage and processing. Camera images may be acquired by an associated camera, or an independent camera situated at a remote location. Processing may be similarly be provided locally on a mobile device, or a remotely at a cloud-based location, or other remote location. Additionally, such processing and storage locations may be situated at a similar location, or at remote locations.

Moreover, the separation of various system modules and components in the embodiments described above should not be understood as requiring such separation in all embodiments, and it should be understood that the described program components and systems can generally be integrated together in a single software product or packaged into multiple software products.

What is claimed is:

1. A computer-implemented method comprising:
   obtaining a video of a subject, the video comprising a plurality of frames;
   generating, based on both a subject portion and a background portion of each frame of the plurality of frames, a plurality of optical flows representing movement in the plurality of frames; and
   providing the plurality of optical flows as inputs to an autoencoder to obtain, as an output of the autoencoder, a representation having a reduced dimensionality compared to the plurality of optical flows, the representation including a movement-based biomarker value of the subject,
   wherein the autoencoder is trained based on comparisons between training optical flows and reconstructed optical flows generated based on autoencoder processing of the training optical flows.

2. The computer-implemented method of claim 1, wherein the movement-based biomarker value comprises a frequency of tremor of the subject.

3. The computer-implemented method of claim 2, wherein the representation comprises a type of tremor of the subject.

4. The computer-implemented method of claim 3, wherein the type of tremor comprises a hand position of the subject.

5. The computer-implemented method of claim 1, wherein the representation comprises a biomarker type corresponding to the movement-based biomarker value.

6. The computer-implemented method of claim 5, wherein the biomarker type comprises a facial muscle group of the subject, and wherein the movement-based biomarker value comprises a measure of intensity of movement of the facial muscle group or a measure of frequency of movement of the facial muscle group.

7. The computer-implemented method of claim 1, further comprising:
   generating a plurality of reconstructed optical flows using an adversarial autoencoder network, the plurality of reconstructed optical flows based on random samples drawn from a prior distribution used to train the autoencoder in an adversarial discrimination process, and training the autoencoder using the plurality of reconstructed optical flows.

8. The computer-implemented method of claim 1, further comprising:
   obtaining a second plurality of optical flows, the second plurality of optical flows being labeled;
   performing one or more of random translation, random rotation, or random scaling on the second plurality of optical flows, to generate an augmenting plurality of optical flows; and
   training the autoencoder using the augmenting plurality of optical flows.

9. The computer-implemented method of claim 1, further comprising training the autoencoder using an adversarial discriminator, comprising:
   comparing, by the adversarial discriminator, the output of the autoencoder to a distribution; and
   updating parameters of the autoencoder based on a difference between the output of the autoencoder and the distribution.

10. The computer-implemented method of claim 1, comprising training the autoencoder using labeled data.

11. The computer-implemented method of claim 10, wherein the labeled data comprises experimentally-derived data, the experimentally-derived data comprising data generated by stimulating a second subject with stimulation having a known frequency.

12. The computer-implemented method of claim 10, wherein the labeled data is labeled with a biomarker type, and
   wherein training the autoencoder comprises training the autoencoder to determine a biomarker value based on implicit training.

13. The computer-implemented method of claim 10, wherein the labeled data is labeled with a biomarker value, and
   wherein training the autoencoder comprises training the autoencoder to determine a biomarker type based on implicit training.

14. The computer-implemented method of claim 1, wherein generating the plurality of optical flows comprises:
   processing the video with one or more of filtering, noise-reduction, or standardization, to generate a plurality of processed video frames; and
   generating the plurality of optical flows based on the plurality of processed video frames.

15. The computer-implemented method of claim 1, comprising generating the plurality of optical flows based on respective pairs of frames of the plurality of frames.

16. The computer-implemented method of claim 1, wherein providing the plurality of optical flows as inputs to the autoencoder comprises providing one or more optical flow maps as inputs to the autoencoder, the optical flow maps generated based on the plurality of optical flows.

* * * * *